US008941828B2

(12) United States Patent
Loock et al.

(10) Patent No.: US 8,941,828 B2
(45) Date of Patent: Jan. 27, 2015

(54) MULTIPLE WAVELENGTH CAVITY RING-DOWN SPECTROSCOPY

(75) Inventors: Hans-Peter Loock, Kingston (CA); Helen Waechter, Warrington, PA (US)

(73) Assignee: Queen's University at Kingston, Kingston, ON (CA)

( * ) Notice: Subject to any disclaimer, the term of this patent is extended or adjusted under 35 U.S.C. 154(b) by 78 days.

(21) Appl. No.: 13/402,207

(22) Filed: Feb. 22, 2012

(65) Prior Publication Data

US 2012/0212731 A1 Aug. 23, 2012

Related U.S. Application Data

(60) Provisional application No. 61/445,396, filed on Feb. 22, 2011.

(51) Int. Cl.
*G01J 3/42* (2006.01)
*G01J 3/45* (2006.01)
*G01J 3/427* (2006.01)
*G01J 3/433* (2006.01)
*G01N 21/77* (2006.01)

(52) U.S. Cl.
CPC .. *G01J 3/42* (2013.01); *G01J 3/427* (2013.01); *G01J 3/433* (2013.01); *G01N 21/7746* (2013.01); *G01N 2021/7776* (2013.01); *G01N 2021/7779* (2013.01); *G01N 2021/7783* (2013.01)
USPC ............. 356/320; 356/437; 356/451; 385/12; 250/227.14

(58) Field of Classification Search
CPC ... G01N 21/39; G01N 21/031; G01N 21/552; G01N 21/3151; G01N 21/7703; G01N 2021/391; G01N 2021/1704; G01N 2021/7789; G01J 3/42; G01J 3/0218; G01J 3/4338; G01J 9/00
USPC ................. 356/451, 484, 454, 432–440, 300; 250/343, 227.14; 385/12, 15
See application file for complete search history.

(56) References Cited

U.S. PATENT DOCUMENTS

| | | | | |
|---|---|---|---|---|
| 5,528,040 | A * | 6/1996 | Lehmann | 250/343 |
| 6,727,492 | B1 * | 4/2004 | Ye et al. | 250/227.18 |
| 7,046,362 | B2 * | 5/2006 | Lehmann et al. | 356/437 |
| 7,369,242 | B2 * | 5/2008 | Cole et al. | 356/436 |
| 7,612,885 | B2 * | 11/2009 | Cole et al. | 356/437 |
| 7,884,938 | B2 * | 2/2011 | Cole | 356/437 |
| 8,437,000 | B2 * | 5/2013 | Cole et al. | 356/437 |
| 2005/0117157 | A1 * | 6/2005 | Tarsa | 356/437 |

(Continued)

OTHER PUBLICATIONS

Waechter, H., et al., "405 nm Absorption Detection in Nanoliter Volumes", Anal. Chem., vol. 81(21), 9048-9054 (2009).

(Continued)

*Primary Examiner* — Hoa Pham

(57) ABSTRACT

Described are methods for multi-wavelength cavity ring-down spectroscopy; comprising simultaneously and continuously irradiating an optical cavity with light at two or more different wavelengths, each light being intensity-modulated at a different modulation frequency, detecting the light of two or more wavelengths after the light has traveled through the optical cavity; measuring an optical loss of each detected light; and determining a characteristic of the optical cavity from the optical loss of each detected light. Also described are apparatus and systems for multi-wavelength cavity ring-down spectroscopy.

19 Claims, 8 Drawing Sheets

(56) References Cited

U.S. PATENT DOCUMENTS

| | | | |
|---|---|---|---|
| 2005/0134836 A1* | 6/2005 | Paldus et al. | 356/73 |
| 2006/0181710 A1* | 8/2006 | Kachanov et al. | 356/437 |
| 2007/0229080 A1* | 10/2007 | Weiss et al. | 324/322 |
| 2007/0252995 A1* | 11/2007 | Shaw | 356/437 |
| 2008/0179530 A1* | 7/2008 | Liu et al. | 250/343 |
| 2010/0154620 A1* | 6/2010 | Loock et al. | 84/724 |
| 2011/0235022 A1* | 9/2011 | Majewski et al. | 356/51 |
| 2011/0317164 A1* | 12/2011 | Cole et al. | 356/437 |
| 2013/0044314 A1* | 2/2013 | Koulikov et al. | 356/72 |

OTHER PUBLICATIONS

Orphal, J., et al., "High-resolution Fourier-transform cavity-enhanced absorption spectroscopy in the near-infrared using an incoherent broad-band light source", Optics Express 16(23), 19232-19243 (2008).

He, Y., et al., "Simultaneous multi-laser, multi-species trace-level sensing of gas mixtures by rapidly swept continuous-wave cavity-ringdown spectroscopy", Optics Express 18(19), 20059-20071 (2010).

Chen, D., et al., "Modulation Frequency Multiplexed Tunable Diode Laser Spectroscopy System for Simultaneous CO, CO2 Measurements", Chin. Phys. Lett. 23(9), 2446-2449 (2006).

Engeln, R., et al., "A Fourier transform cavity ring down spectrometer", Rev. Sci. Instrum. 67(8), 2708-2713 (1996).

Gerard, Y., et al., "Multispecies in situ monitoring of a static internal combustion engine by near-infrared diode laser sensors", Applied Optics 46(19), 3937-3945 (2007).

Gianfrani, L., et al., "Isotope analysis of water by means of near-infrared dual-wavelength diode laser spectroscopy", Optics Express 11(13), 1566-1576 (2003).

Hamers, E., et al., "Fourier transform phase shift cavity ring down spectroscopy", Chemical Physics Letters 365, 237-243 (2002).

He, Y., et al., "Rapidly swept, continuous-wave cavity ringdown spectroscopy with optical heterodyne detection: single-and multi-wavelength sensing of gases", Applied Physics B 75, 267-280 (2002).

Loock, H.-P., et al., "Chemical microanalysis with cavity-enhanced optical waveguide devices", Proc. SPIE vol. 8332, 833204-1-13 (2011).

Waechter, H., et al., Simultaneous and Continuous Multiple Wavelength Absorption Spectroscopy on Nanoliter Volumes Based on Frequency-Division Multiplexing Fiber-Loop Cavity Ring-Down Spectroscopy, Anal. Chem 83(7), 2719-2725 (2011).

Bescherer, K., et al., "Measurement of multi-exponential optical decay processes by phase-shift cavity ring-down", Applied Physics B 96, 193-200 (2009).

Engeln, R., et al., "Phase shift cavity ring down absorption spectroscopy", Chem. Phys. Lett. 262, 105-109 (1996).

Barnes, J., et al., "Loss determination in microsphere resonators by phase-shift cavity ring-down measurements", Optics Express 16(17), 13158-13167 (2008).

Johnston, P.S., et al., "Cavity enhanced absorption spectroscopy using a broadband prism cavity and a supercontinuum source", Optics Express 16(19), 15013-15023 (2008).

Ruth, A.A., et al., "Fourier-transform cavity-enhanced absorption spectroscopy using an incoherent broadband light source", Appl. Opt. 46(17), 3611-3616 (2007).

Adler, F., et al., "Cavity-enhanced direct frequency comb spectroscopy: Technology and Applications", Annu. Rev. of Anal. Chem., 3, 175-205 (2010).

Oh, D.B., et al., "Frequency modulation multiplexing for simultaneous detection of multiple gases by use of wavelength modulation spectroscopy with diode lasers", Appl. Opt. 37(12), 2499-2501 (1998).

Yu, G., et al., "Frequency-domain multiplexing system for in vivo diffuse light measurements of rapid cerebral hemodynamics", Appl. Opt. 42(16), 2931-2939 (2003).

Loock, H.-P., "Ring-down absorption spectroscopy for analytical microdevices", Trends Anal. Chem., 25(7), 655-664 (2006).

* cited by examiner

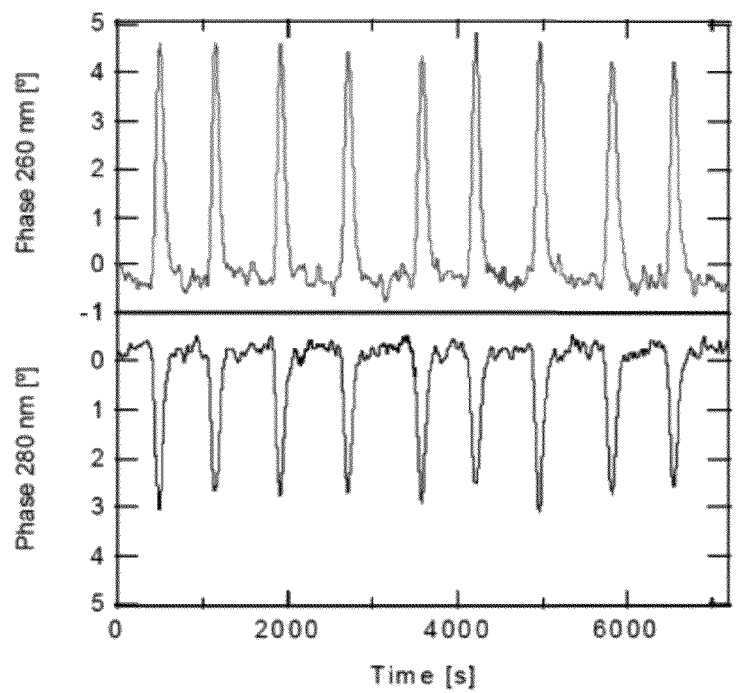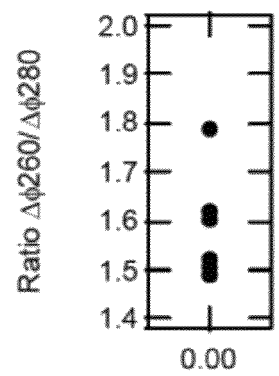
Figure 8(a)                    Figure 8(b)

MULTIPLE WAVELENGTH CAVITY RING-DOWN SPECTROSCOPY

RELATED APPLICATION

This application claims the benefit of the filing date of U.S. Provisional Patent Application No. 61/445,396; filed on Feb. 22, 2011, the contents of which are incorporated herein by reference in their entirety.

FIELD

This invention relates to spectroscopy. In particular, this invention relates to methods and apparatus for fast, sensitive measurements of small samples using multiple wavelength cavity ring-down spectroscopy.

BACKGROUND

Cavity ring-down (CRD) spectroscopy is an established method for sensitive absorption spectroscopic measurements in gaseous and liquid samples. Extremely sensitive measurements on liquid samples can be performed by filling a conventional cavity with liquid sample, but for many applications in analytical spectroscopy a smaller sample volume is preferred. A cavity of microliter dimensions may be made by reducing the distance between the cavity mirrors to millimeters. Alternatively, one can insert either a cuvette or flow cell, or a liquid film into a larger two-mirror cavity. Another possibility is to use total internal reflection as a third cavity mirror and probe the sample with the evanescent wave. Even smaller volumes of less than 1 μL can be interrogated by using a fiber optic waveguide as the cavity medium.

CRD spectroscopy (CRDS) using a fiber loop is similar to mirror-based CRDS in that the measured ring-down time describes the losses of the fiber-loop cavity containing the sample. While the loss term of interest is the absorption due to the sample, in a fiber cavity there are additional losses due to absorption in the optical fiber, $\alpha_{fiber}$, and losses at splices and at the sample gap. The ring-down time of a fiber loop with length L, sample gap width d and round trip time $t_{RT}$ is given by:

$$\tau = \frac{t_{RT}}{\text{losses}} = \frac{nL}{c(-\ln(T_{gap,splice}) + \alpha_{fiber}L + C\tilde{\varepsilon}d)} \quad (1)$$

The term $-\ln(T_{gap,splice})$ describes the losses per roundtrip due to the sample gap and fiber splices, C is the concentration of the sample, $\tilde{\varepsilon}$ is the molar extinction coefficient of the sample based on the natural logarithm (related to the decadic extinction coefficient by $\tilde{\varepsilon}=\varepsilon \cdot \ln(10)$), c is the vacuum speed of light and n is the effective refractive index of the propagating modes.

There are several ways of determining the ring-down time. For example, in pulsed or in continuous wave (cw) CRD spectroscopy the decay of the light intensity is monitored as a function of time. In phase-shift CRD spectroscopy the intensity of the laser is modulated sinusoidally and the cavity emits light that is phase-shifted due to the lifetime of the photons in the cavity, i.e. the ring-down time. The ring-down time can then be obtained by measuring the phase-shift $\Delta\phi$ between the light entering and exiting the cavity at modulation frequency $\omega=2\pi\nu$:

$$\tan(\Delta\phi)=-\omega\tau \quad (2)$$

For a single-exponential decay there is a linear relationship between the ring-down time τ, the tangent of the phase-shift $\Delta\phi$ and the modulation frequency ω (see equation 2). For multi-exponential decays the relationship between $\tan \Delta\phi$ and τ is no longer linear:

$$\tan(\Delta\phi) = -\omega \frac{\sum_{j=1}^{N} \frac{\alpha_j \tau_j^2}{\omega^2 \tau_j^2 + 1}}{\sum_{j=1}^{N} \frac{\alpha_j \tau_j}{\omega^2 \tau_j^2 + 1}} \xrightarrow{N=2} \tan(\Delta\phi) \quad (3)$$

$$= -\omega \frac{\frac{\tau_1^2}{\omega^2 \tau_1^2 + 1} + \frac{\alpha_{2,1} \tau_2^2}{\omega^2 \tau_2^2 + 1}}{\frac{\tau_1}{\omega^2 \tau_1^2 + 1} + \frac{\alpha_{2,1} \tau_2}{\omega^2 \tau_2^2 + 1}},$$

$$\alpha_{2,1} = \frac{\alpha_2}{\alpha_1}$$

The ring-down times can nevertheless be determined by measuring the phase-shift at several modulation frequencies. In optical fibers bi-exponential or tri-exponential decays are observed frequently, since the light is traveling not only in the core but also in the cladding and coating.

SUMMARY

Described herein is a method for simultaneous and continuous multi-wavelength cavity ring-down spectroscopy. The method may comprise simultaneously and continuously irradiating an optical cavity with light at two or more different wavelengths, each light being intensity-modulated at a different modulation frequency; detecting the light of two or more wavelengths after the light has traveled through the optical cavity; measuring an optical loss of each detected light; and determining optical loss of the optical cavity. The optical loss may be related to the absorption spectrum of a sample inserted into the cavity or to an external stimulus acting on one or more sensor elements in the cavity (e.g., a mechanical, thermal, optical, chemical, or other stimulus). The optical cavity may comprise an optical fiber loop, a fiber Fabry-Perot cavity, a mirror cavity, a micro-photonic resonator, or a prism cavity. In one embodiment the method may comprise measuring phase shift between light entering and exiting the optical cavity for each of the two or more modulation frequencies.

The method may comprise frequency-division multiplexing of the light at two or more different wavelengths.

In one embodiment, the optical cavity may include at least one sensor element, wherein optical transmission of the at least one sensor element changes as a function of an external stimulus. The change in optical transmission may be a change in refractive index or optical absorption or optical scattering. The external stimulus may be physical, such as strain or pressure, or chemical. The at least one sensor element may be selected from an absorption cell, a long period grating, an evanescent field block, an interferometer, and a gap in an optical fiber.

The absorption cell may comprise a gap in an optical path of the light at two or more different wavelengths, wherein the method includes disposing a sample in the gap; the sample having an optical absorption spectrum in a spectral region of the light at two or more different wavelengths. The method may comprise measuring absorption of the sample at the two or more wavelengths, wherein absorption is indicative of presence and/or concentration of at least one analyte in the sample.

Also described herein is an apparatus and a system for carrying out simultaneous and continuous multi-wavelength cavity ring-down spectroscopy as described herein.

In one embodiment a system for multi-wavelength cavity ring-down spectroscopy; comprises an optical cavity; two or more light sources of different wavelengths, each light being intensity-modulated at a different modulation frequency; a detector that detects the light of two or more wavelengths after the light has traveled through the optical cavity; means that measures an optical loss of each detected light; and means that determines optical loss of the optical cavity from each detected light.

The optical cavity may comprise an optical fiber loop, a fiber Fabry-Perot cavity, a mirror cavity, a micro-photonic resonator, or a prism cavity. The optical cavity may include at least one sensor element, wherein optical transmission of the at least one sensor element changes as a function of an external stimulus.

The system may include at least one sensor element selected from an absorption cell, a long period grating, an evanescent field block, an interferometer, and a gap in an optical fiber. In one embodiment, the absorption cell may comprise a gap in an optical path of the light at two or more different wavelengths, the gap accommodating a sample disposed therein. The sample may have an optical absorption spectrum in a spectral region of the light at two or more different wavelengths.

In the methods, apparatus, and systems described herein, the sample may be a gas, liquid, solid, or solid suspension. The light sources may be lasers, light emitting diodes (LEDs), or other light-emitting devices, or combinations thereof, wherein peaks of the emission spectra are different for each light source. Preferably the emission spectra do not substantially overlap. The wavelengths may be in the UV-range, e.g., by using UV-emitting LEDs. The number of simultaneously detected wavelengths may be increased by coupling several light sources into the optical cavity. Lock-in amplifiers or phase comparators may be used.

As described herein, ring-down time may be measured at two or more wavelengths using intensity modulated light from respective two or more light sources each modulated at a different modulation frequency, by measuring the phase shift between the light entering and exiting the optical cavity. Wavelength-specific optical loss may be obtained by referencing a total detected signal against the different modulation frequencies. Modulation frequencies may be chosen such that neither they, nor their low-order harmonics, are close to each other, i.e., they are not within a detection band of a phase comparator used to measure the phase shift. For maximal sensitivity the modulation frequencies may be chosen such that they are on the order of $2\pi$/ring-down time.

BRIEF DESCRIPTION OF THE DRAWINGS

For a better understanding of the invention, and to show more clearly how it may be carried into effect, embodiments will be described, by way of example, with reference to the accompanying drawings, wherein:

FIG. 8(a) is a plot showing phase shift measurements at λ=260 nm and 280 nm during multiple injections of ketoprofen (15 µg/mL). FIG. 8(b) shows the Δφ260/Δφ280 ratio is 1.6 with a standard deviation of 0.1.

DETAILED DESCRIPTION OF EMBODIMENTS

Figure 1A:
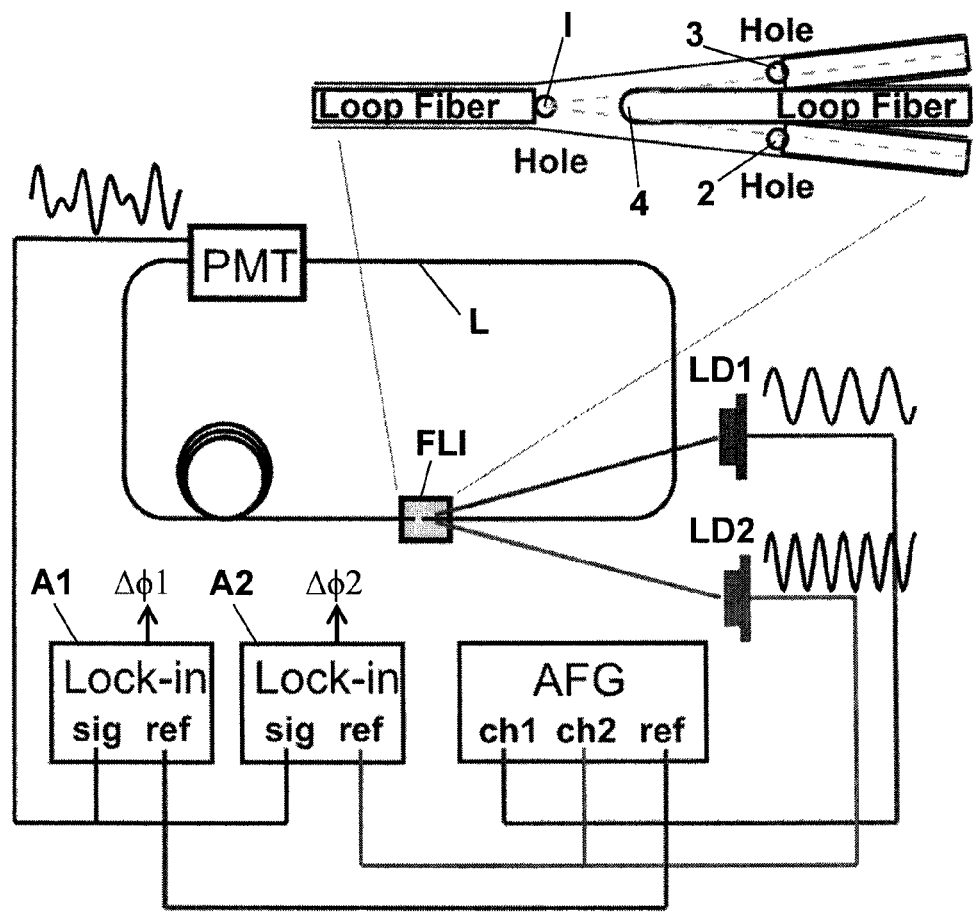
FIG. 1(a) is a block diagram of a multi-wavelength phase-shift CRD system according to one embodiment of the invention.

The methods described herein provide multi-wavelength cavity ring-down spectroscopy, wherein an optical cavity is simultaneously and continuously irradiated with light at two or more different wavelengths, each light being intensity-modulated at a different modulation frequency. The light at two or more wavelengths is detected after it has traveled through the optical cavity, and the optical loss of the detected light at each modulation frequency is measured. Based on this measurement, the optical loss of the optical cavity is determined. The optical loss may be related to the absorption spectrum of a sample inserted into the cavity or to an external stimulus acting on one or more sensor elements in the cavity (e.g., a physical, chemical, or other stimulus). In one embodiment the optical loss is measured by measuring phase shift of the detected light at each modulation frequency.

The optical cavity may be an optical fiber loop, a fiber Fabry-Perot cavity, a mirror cavity, a micro-photonic resonator, or a prism cavity, or may include at least one sensor element. For example, at least one sensor element that changes its optical transmission as a function of an external stimulus may be used. Examples of such sensor elements include, but are not limited to, an absorption cell, a long period grating, an evanescent field block, an interferometer, and a gap in an optical fiber. In one embodiment the absorption cell comprises a gap in an optical path of the light. A liquid, gas, or suspended solid sample may be disposed in the gap, and one or more analytes in the sample may be identified and/or characterized based on its optical absorption spectrum in a spectral region of the light at two or more different wavelengths. For example, measuring absorption of the sample at the two or more wavelengths provides an indication of presence and/or concentration of at least one analyte in the sample.

In one embodiment, the methods described herein take advantage of the broad wavelength range that is accessible with silica waveguide cavities (about 250-1700 nm) by applying fiber-loop CRDS techniques to simultaneous and continuous dual-wavelength (or multi-wavelength) detection. In phase-shift CRDS the ring-down time is obtained from the phase-shift between intensity modulated light entering and exiting the cavity. Using multiple light sources that are modulated at different frequencies permits distinguishing the wavelengths by demultiplexing the output of a single broadband photodetector. The detector records the total output of the cavity, i.e., there is no need to disperse the wavelengths.

Related methods of broadband CRD spectroscopy include time-division multiplexing of ring-down signals, Fourier transform CRDS, as well as cavity enhanced absorption spectroscopy (CEA) with a wavelength dispersive element. However, multi-wavelength CRD spectroscopy has not previously been conducted with quasi-continuous light sources and without a dispersive element or interferometer.

In one embodiment, simultaneous multi-wavelength detection without a dispersive element is achieved by combining phase-shift CRD spectroscopy with frequency-division multiplexing. As a demonstration, light at two different wavelengths from two lasers sources was coupled into a fiber cavity, and each was intensity modulated at a distinct frequency, co. A single broadband detector recorded the wavelengths simultaneously and the output was directed to two separate lock-in amplifiers which demodulated the total signal at their respective modulation frequencies to extract the phase information. The phase-shift between input and output contains information about the ring-down time at the specific wavelength.

Embodiments described herein are different from the frequency modulation multiplexing technique for wavelength-modulation spectroscopy, suggested by others. In that previous work, a number of light sources were modulated simultaneously at different frequencies to perform wavelength-modulation spectroscopy at multiple wavelengths. A single, broadband detector recorded the total intensity of the three-or-more light sources after a single pass through the sample gas. The signal was demultiplexed by sending the detector output to three-or-more mixers, which were each referenced to one of the modulation frequencies. In these previous cases the wavelength of each laser was modulated at a different frequency but their intensity was constant. In contrast, in embodiments described herein, the intensity is modulated but the wavelength of each laser is constant. Furthermore, whereas the former method is strictly applicable only to absorption features that are quite narrow, such as absorption lines associated with rotational, rovibrational, and rovibronic transitions, the embodiments described herein are also applicable to spectra that are broadened by, e.g., solvent or matrix environments.

Of concern when measuring several wavelengths simultaneously is the amount of crosstalk between different channels. For example, a sudden change in the modulation amplitude A(t) creates new frequencies, which might lead to crosstalk. However, in the embodiments described herein the amplitude change is so slow that broadening in the frequency does not overlap with the modulation frequency of the other laser. Also, a phase change ϕ(t) caused, for example, by a sudden appearance of an analyte may create new frequencies. Again, the change is on the time scale of seconds and too slow for crosstalk to occur. In the present embodiments the modulation frequencies are separated by a few hundred kHz, whereas phase changes and amplitude changes give a frequency change in the mHz range.

The most important source for crosstalk is due to imperfect electronic instruments. If the modulation of the laser intensity is not a pure sine wave but also contains other frequencies, a component of the signal may be observable at the modulation frequency of the other laser. However, only very small contributions (<3%) of higher harmonics were observed in the present work. Also, saturation effects and nonlinear response of the detector may lead to distortion of the signal, which can result in crosstalk. Therefore, as a precaution the frequencies are selected such that higher harmonics of one modulation frequency are not close to the one or more other modulation frequencies (or their harmonics).

If the electronic instruments and cables of the two lasers and detector are not properly shielded and grounded, there might be crosstalk between the laser drivers or between cables due to capacitive coupling, inductive coupling, or ground loops. Also, the lock-in amplifier used to measure the phase is a source for crosstalk. The filter for rejecting other frequencies has a certain bandwidth (0.26 Hz, for example), and frequency components close to the measured frequency may contribute to the phase signal. Therefore, modulation frequencies were spread apart by considerably more than the filter bandwidth.

An embodiment of a phase-shift CRD system is shown in FIG. 1(a), and includes a fiber loop L (L=9.25 m, n=1.44), two laser diodes LD1, LD2, a photomultiplier tube PMT (Hamamatsu, R955), two lock-in amplifiers A1, A2, an arbitrary function generator AFG, and a fiber-liquid interface FLI. In this embodiment the fiber is a low-loss UV fiber (CeramOptec, Optran UV, core diameter: 400 μm, cladding diameter: 425 μm) with an absorption coefficient of $\alpha_{fiber}$=0.011 m$^{-1}$ at 405 nm and $\alpha_{fiber}$=0.0011 m$^{-1}$ at 810 nm.

Referring to FIG. 1(a), the PMT was placed in contact with the fiber loop to record the intensity of the light in the loop. The light source LD1 was a diode laser with a wavelength of 405 nm (Nichia, NDHV310APC, power: 65 mW before fiber coupling, 30 mW after fiber coupling), and the light source LD2 was a diode laser with a wavelength of 810 nm (JDSU, SDL-2372, power: 2 W before fiber coupling). Despite the considerable higher power of the 810 nm laser, the signal measured in the fiber loop was higher only by a factor of five for the 810 nm laser compared to the 405 nm laser because of the lower fiber coupling efficiency of the 810 nm laser and the lower sensitivity of the PMT at 810 nm. The diode lasers were modulated at a different modulation frequencies $\omega_i$ using the function generator AFG (Tektronix, AFG 3022B). The broadband detector PMT measured both wavelengths simultaneously. The signal from the PMT was divided and directed to the two lock-in amplifiers A1, A2 (Stanford Research System, SRS844, time constant 300 ms). By directly modulating the laser current the 405 nm diode laser was amplitude modulated with a frequency of 2.3 MHz, and the 810 nm diode laser was modulated with 1.9 MHz.

The sample was injected into the fiber-liquid interface using a sample injector (Rheodyne; sample volume of 5 μL) into a flow of solvent (water or phosphate buffer at pH 7.2) with a flow rate of 10 μL/min.

Figure 1B:
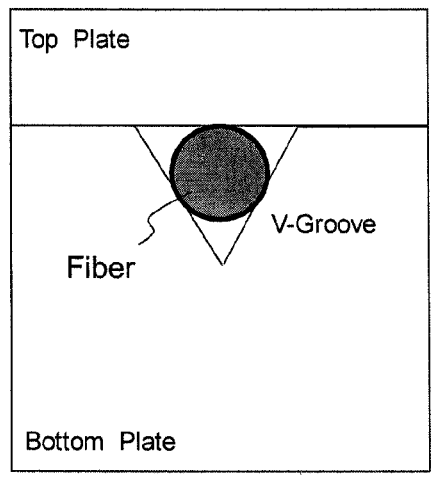
FIG. 1(b) is a drawing of a cross-section of the fiber-liquid interface showing the V-groove used to align the optical fibers.

The fiber-liquid interface FLI, shown in detail in the inset in FIG. 1(a) and in cross-section in FIG. 1(b), was an improved version of an interface described earlier (Waechter, H., et al., Anal. Chem. 2009, 81, 9048-9054). It defines the sample flow path, keeps the fiber ends in place and couples light into the fiber loop. The interface was made of two plates of cyclic olefin copolymer (COC, Zeonor, 1420R Grade) containing V-grooves for the fibers. The liquid entered the interface through a hole 1 in the bottom plate, flowed between the loop fiber ends, along the grooves to the delivery fiber ends, and exited the interface through the two holes 2, 3 in the top plate (see FIG. 1(a) inset). A spherical lens 4 (radius of curvature ca. 220 μm) was fabricated at one of the fiber ends (by WT&T, Inc.) to increase transmission across the sample gap. For the highest sensitivity the optimal gap width in the fiber loop was determined to be 800 giving a detection volume of about 100 nL. A nanoport (Rheodyne) was glued to the hole in the bottom plate to connect the interface with glass capillaries for a sample flow. Details on the fabrication process are provided in Example 1.

Two different substances were used for the absorption measurements: tartrazine (Fluka; purity not specified) and ADS830WS (American Dye Solution Inc.; purity not specified). Tartrazine samples were prepared in distilled water and in phosphate buffer (pH 7.2, Ricca Chemical Company); ADS830WS samples were only prepared in distilled water, since the dye has a low solubility in phosphate buffer. Tartrazine has a strong absorption feature around 410 nm ($\epsilon=22660$ L mol$^{-1}$cm$^{-1}$, decadic extinction coefficient) and is largely transparent at 810 nm. ADS830WS has a strong absorption feature around 830 nm ($\epsilon=50050$ L mol$^{-1}$cm$^{-1}$ at 810 nm) but also a weaker absorption at 405 nm ($\epsilon=6450$ L mol$^{-1}$cm$^{-1}$).

Figure 5:
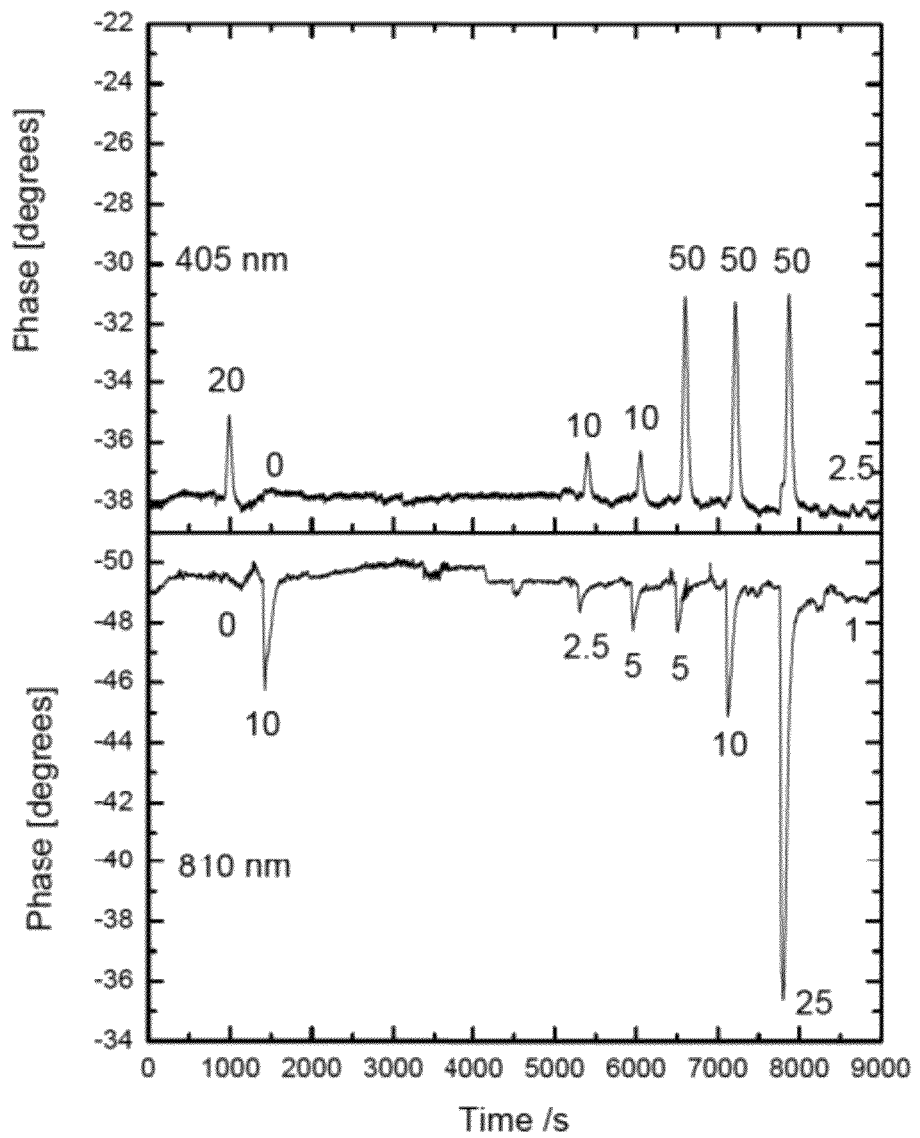
FIG. 5 is a plot showing phase-shift at 405 nm and 810 nm with different concentrations of pure ADS830WS and tartrazine, and mixtures of both (concentrations in µM: top, tartrazine; bottom, ADS830WS) (note that the vertical axis in the lower panel is reversed for clarity).
Figure 6:
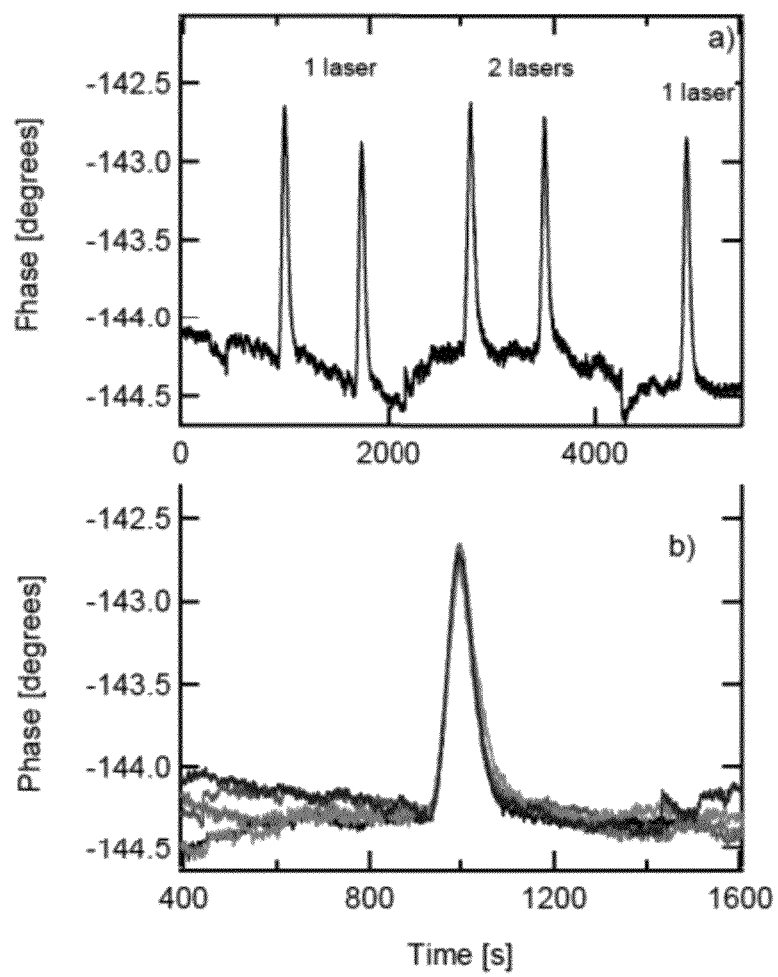
FIGS. 6(a) and 6(b) are plots showing measurement of tartrazine (10 µM concentration), (a) with both lasers on and with only the 405 nm laser on, and (b) with measurements overlaid.

To demonstrate simultaneous detection at two wavelengths without substantial crosstalk, the system of FIG. 1(a) was tested using several combinations of lasers and dyes, i.e., the concentration of each dye was quantified separately and in mixtures of both dyes, using either both lasers together or separately. The concentration of tartrazine was varied from 1.0-500 μM, and for ADS830WS from 1.0-100 μM. The following measurements were performed:

1. 405 nm laser and 810 nm laser simultaneously, tartrazine samples (FIGS. 2(a)-(d));
2. 405 nm laser and 810 nm laser simultaneously, ADS830WS samples (FIGS. 2(e)-(h));
3. 405 nm laser and 810 nm laser simultaneously, ADS830WS and tartrazine samples and mixtures of both (FIG. 5);
4. 405 nm laser, 810 nm laser on and off, tartrazine sample (FIGS. 6(a) and (b)); and
5. 810 nm laser on, 405 nm laser on and off, ADS830WS samples (not shown).

Figure 4:
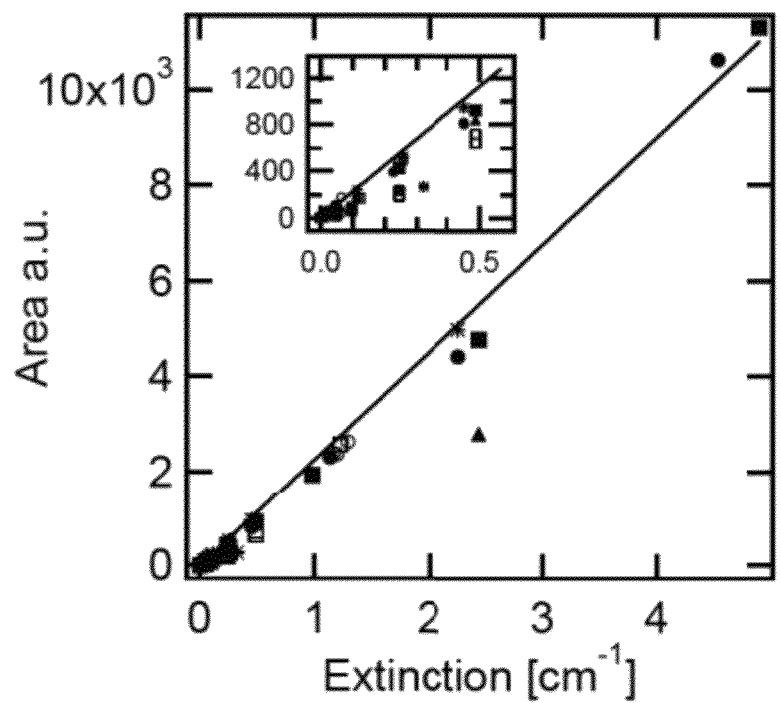
FIG. 4 is a plot showing area of converted sample peaks versus extinction: black circles, tartrazine measured at 405 nm; black squares, ADS830WS at 810 nm; stars, mixtures at 405 nm; triangles, mixtures at 810 nm; open circles, mixtures at 405 nm (FIG. 5); open squares, mixtures at 810 nm (FIG. 5); line, fit to the tartrazine data recorded at 405 nm; inset shows the data at small extinction values.

Measurements 1 and 2 were used to determine the detection limit and for calibration of the system (FIGS. 2(a)-(h) and 3). The amount of crosstalk was studied in measurements 3, 4 and 5 and by comparing the sample peaks from measurements 1 to 3 with each other (FIG. 4).

Figure 2:
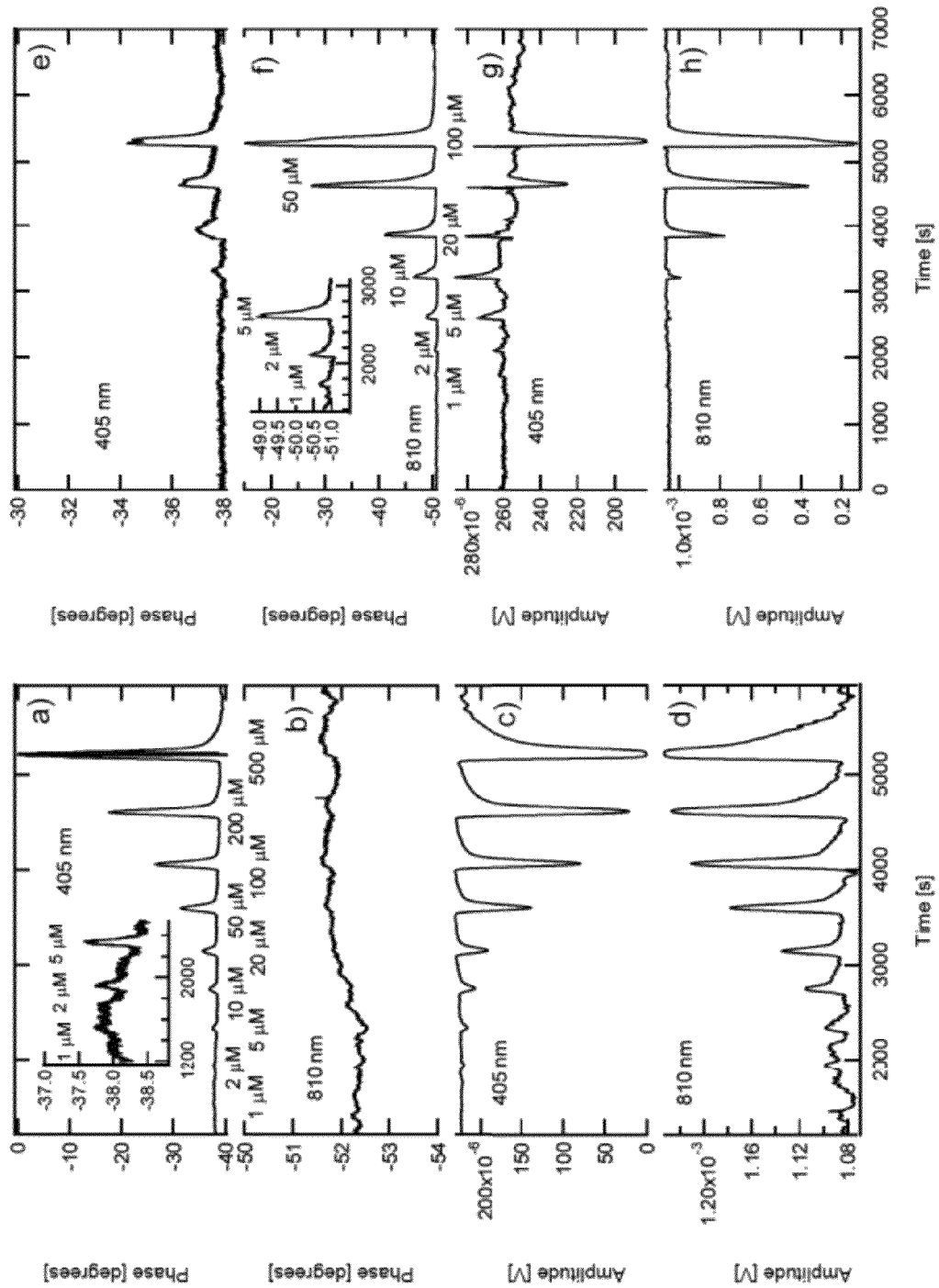
FIGS. 2(a)-(f) are plots of phase shift and amplitude of the laser light intensities using different samples: (a) phase shift at 405 nm at different sample concentrations of tartrazine (at 500 µM all the light is absorbed before it is coupled into the fiber loop, indicating the upper limit of the detection system); (b) phase shift at 810 nm at different sample concentrations of tartrazine; (c) amplitude of the 405 nm laser light intensity; (d) amplitude of the 810 nm laser light intensity; (e) phase shift at 405 nm at different sample concentrations of ADS830WS; (f) phase shift at 810 nm at different sample concentrations of ADS830WS.
FIG. 2(g) is a plot of amplitude of the 405 nm laser light intensity.
FIG. 2(h) is a plot of amplitude of the 810 nm laser light intensity.
Figure 3:
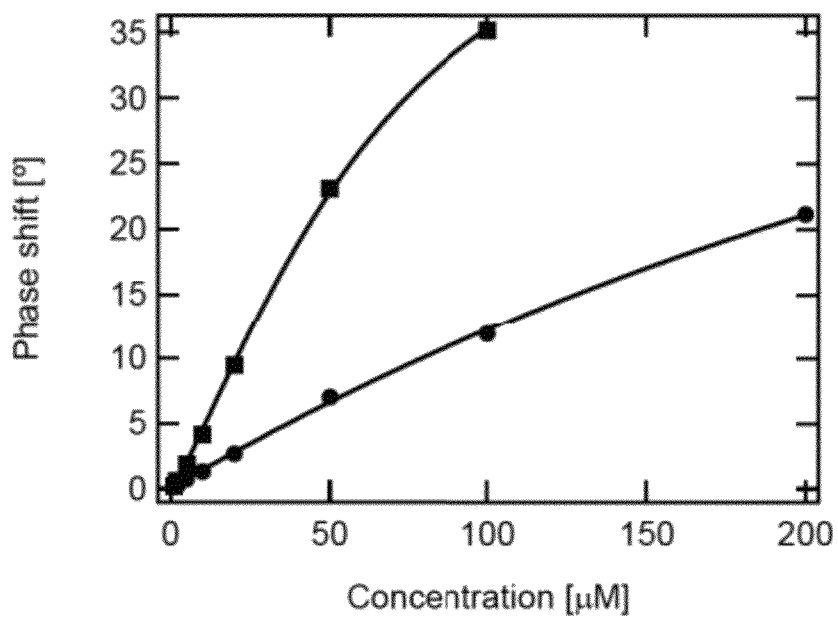
FIG. 3 shows calibration curves used to convert phase-shift into concentrations: circles, tartrazine, sample volume 50 µL, flow rate 10 µL/min; squares, ADS830WS, sample volume 5 µL, flow rate 10 µL/min; lines, fit with equation 3 (bi-exponential decay). The precision of the phase-shift measurement is 0.04 degrees at 405 nm and 0.2 degrees at 810 nm, the accuracy of the concentration is estimated to be 1%.

Tartrazine samples change only the phase of the 405 nm signal but not the phase at 810 nm, as expected (see FIGS. 2(a) and (b)). ADS830WS samples introduce mainly a change in the phase of the 810 nm and also a small change at 405 nm due to its weak absorption at this wavelength (see FIGS. 2(e) and (f)). The amplitude read-out, however, responded to the sample injections at both laser wavelengths (see FIGS. 2(c), (d), (g) and (h)). It is suggested herein that the amplitude of one of the laser signals changes due to saturation effects of the detector introduced by the other laser, i.e., as the intensity of the 405 nm laser light decreases during tartrazine measurements, the detector response increases slightly and therefore the signal amplitude of the signal of the 810 nm laser appears to increase, and vice versa. The effect may be avoided by using a detector that has a larger linear response region.

For ADS830WS samples, the amplitude of the 810 nm laser signal decreases with increasing concentration, while the amplitude of the 405 nm laser signal either increases or decreases depending on the concentration of the sample. At low concentration the amplitude is increased because of the decrease of the 810 nm amplitude (saturation effect of the detector), whereas at higher concentrations the 405 nm amplitude decreases due to absorption. This effect does not affect the concentration measurement because only the phase-shift is used to extract the concentration.

Using an integration-time of 300 ms the detection limit (3 times standard deviation of baseline noise) at 405 nm is 0.9 μM of tartrazine. This corresponds to an absorption coefficient of 0.020 cm$^{-1}$ or 0.037 cm$^{-1}$Hz$^{-1/2}$, respectively. The upper detection limit is given by the attenuation of the injected laser light by the sample in the interface and is about 500 μM of tartrazine or 11 cm$^{-1}$, respectively (FIG. 2(a)). At this concentration the light coming from the delivery fiber is greatly attenuated before it reaches the receiving fiber facet. The detection limit for ADS830WS at 810 nm is 1 μM (0.05 cm$^{-1}$), i.e., slightly poorer compared to 405 nm even though the ring-down time at 810 nm is comparable to that at 405 nm. The poorer detection limit is related to the larger fluctuation of the baseline due to the noisier 810 nm laser driver.

To verify accuracy of the tartrazine and ADS830WS concentrations obtained by dual-wavelength phase-shift CRD as described herein, the observed peak areas were compared to the extinction $\epsilon \cdot C$, which was calculated from the absorption coefficient and the injected concentration. The peak area cannot be obtained directly from the phase-shift measurements in FIGS. 2(a), (b), (e), and (f) because the relationship between concentration and phase-shift is not linear (see FIG. 3 and equations (2) and (3)). A calibration curve was therefore used to convert the phase-shift into concentration and the resulting peak areas were obtained by numerical integration. The calibration curve was measured using larger sample volumes, e.g., 50 μL for tartrazine (flow rate 10 μL/min) and 200 μL for ADS830WS (flow rate 50 μL/min). For the latter the same peak heights were obtained with a sample volume of 5 μL and 200 μL, indicating that peak broadening due to diffusion or mixing does not substantially influence the peak concentration. The peak height values from the 4 μL sample volume measurements were used to obtain the calibration curve for ADS830WS from a fit of the data in FIG. 3 to equation (3).

In FIG. 4 the areas of the converted peaks are shown in their dependence on the extinction, $\epsilon \cdot C$. The area relates linearly to the extinction and the measurements of both substances and both wavelengths were in good agreement with each other. The detection system had good reproducibility of 11% (20 μM tartrazine) at 405 nm and 14% (20 μM ADS830WS) at 810 nm. The peak heights had higher reproducibility compared to the peak areas, i.e., 3.3% for tartrazine at 405 nm and 11% for ADS830WS at 810 nm. The reproducibility was determined by taking the standard deviation of the values of ten measurements.

Simultaneous detection at two wavelengths allows distinguishing substances, even if they are mixed in the same sample. This was verified by injecting samples containing only one of the dyes as well as samples with both dyes (see FIG. 5). From the change in the phase shift the concentration in these samples was determined by comparing the response of the mixed samples with one of the pure samples. The response was the same for the same concentration of a substance, regardless whether it is part of a mixture or a pure sample (see FIG. 4).

Another way to test the amount of crosstalk is to compare measurements obtained with only one laser or with both lasers (see FIG. 6(a)). Using the lasers simultaneously slightly increases noise compared to single-wavelength operation. This is attributed to the division of the detector signal between the two lock-in amplifiers which results in a smaller signal amplitude. Also the baseline changes slightly if two lasers are operating compared to only one laser (see FIG. 6(a)). On the other hand, the change in phase lag caused by an analyte plug is very similar regardless whether one or both lasers are turned on. This can be seen more clearly when the peaks are overlaid (see FIG. 6(b)).

The invention is further described by way of the following non-limiting examples.

Example 1

Fabrication of the Fiber-Liquid Interface

Preparation

The fiber-liquid interface was an improved version of an interface described earlier (Waechter, H., et al., Anal. Chem. 2009, 81, 9048-9054). Cyclic olefin copolymer (COC) was used for better chemical resistance, and fibers with core diameters of 400 µm were used. Two delivery fibers were used for dual-wavelength detection.

V-grooves were used because the V-shape of the grooves pre-aligns the fibers. V-grooves were imprinted into the bottom plate with a hot embosser (Jenoptik Mikrotechnik GmbH, HEX01; Temperature: 138° C., force 2000 N for 600 s) and a steel negative (EDM Department Inc.) with the required pattern (see FIG. 1(a)-(b)). The groove in the center holds the fiber loop ends, and the other two grooves, at an angle of 6°, hold the delivery fibers. Holes 1,2,3 of 250 µm diameter were drilled to admit and drain the sample flow. The entrance hole 1 was in the center of the bottom plate at the position of the loop fiber end, and the exit holes 2,3 in the top plate at the position of the delivery fiber ends (see FIG. 1(a)). The top and bottom plates were affixed with a two-component epoxy (Epo-Tek 305), which bonds well to COC and has good chemical resistance (as tested by exposure to water and acetonitrile). A nanoport (Rheodyne) was attached at the entrance hole with the same epoxy. The exit holes could also be connected with nanoports but were left open while aligning the fibers inside the interface.

One end of the loop fiber was rounded to a spherical lens 4 (WT&T Inc.), while the other fiber end and the delivery fiber ends were polished flat perpendicular to the fiber axis. All fiber ends were carefully aligned to achieve the highest sensitivity (see below). Afterwards, UV-curable epoxy (Norland Optical Adhesive 68) was applied at the edge of the interface and dispersed into the grooves by capillary action. When the required part was filled with epoxy, the UV-curing lamp was turned on to stop the flow and to cure the epoxy.

Optimization

Alignment of the loop fiber ends is critical to achieve good performance of the detection system, because this determines the ring-down time and therefore sensitivity of the system. Better axial alignment leads to better transmission across the sample gap, reducing losses in the fiber cavity. One would expect that the lowest losses are obtained when the loop fiber ends are perfectly axially aligned with each other. However, it was observed that a larger phase-shift is obtained if one loop fiber end is slightly shifted to one side. It is suggested herein that this effect might arise because a slight misalignment couples light preferably into modes that have a larger amount of intensity in the center of the fiber. Such modes usually have a higher transmission across the sample gap compared to modes with more intensity at the edge of the fiber core. Therefore a small axial misalignment was found to increase the ring-down time. This may complicate implementing two delivery fibers on the left and right sides from the loop fiber, since the optimal alignment can only be achieved for one delivery fiber at a time. For example, if the fiber ends are optimally aligned for the delivery fiber from the right side, a phase-shift of 45.0° is achieved for this side (405 nm laser), whereas for the other delivery fiber only 21.0° is achieved (810 nm laser). By optimizing for the left delivery fiber a phase-shift of 50° is achieved, but only 16° for the right side. In order to have good performance for both input fibers the middle position may chosen, with a phase-shift that is slightly smaller than for the corresponding optimal position (phase-shift 37° for both sides).

The gap width is selected to maximize the sensitivity of the experiment. While the optical loss may be smallest at very short gap between the fiber ends, the change of optical loss when an absorbing sample is introduced is also small due to the small absorption path length in the sample. In the present embodiment, in which one fiber contains a spherical lens, it is expected that the distance of highest transmission is not at "zero gap width", but at a distance for which the beam waist falls into the acceptance cone of the receiving fiber. The distance of highest sensitivity is expected to be even larger.

To obtain the distance of highest transmission the phase-shift was measured with a diode laser at 405 nm (modulation frequency: 2 MHz). The interface was filled with phosphate buffer pH 7.2 (flow rate: 50 µL/min) for this measurement. The phase-shift depends slightly on the refractive index of the liquid in the sample gap because of the dependence of the focus of the lense on the fiber end on the sample's refractive index. This should not have a considerable influence as long as only aqueous solutions are used. Phase shifts were given with respect to the phase at infinite optical loss, i.e., when the fiber ends were more than 5.38 mm apart. Then the phase shift was measured at gap widths between 0 mm and 4 mm. The maximum phase shift and highest transmission were found at a gap width of 240 µm. In addition, the ring-down time was determined for several gap widths by scanning the modulation frequency from 30 kHz to 4 MHz. From a fit to equation (3) the ring-down times in core and cladding were extracted.

To obtain the gap width of highest sensitivity, the experiment was repeated with three different concentrations of tartrazine in phosphate buffer. A long ring-down time is usually associated with a high sensitivity, because it corresponds to a longer effective absorption path length $d_{eff} = d \cdot \tau / t_{RT}$. Also, a larger gap width, d, increases the effective path length, but for the current embodiment, at distances above 240 µm the ring-down time decreased due to increasing transmission losses. Based on this, the highest sensitivity is obtained at distances greater than 240 µm but less than about 2 or 3 mm.

The gap width of highest sensitivity was obtained by subtracting the phase-shift of pure phosphate buffer from that of an absorbing sample. The highest sensitivity was found at a gap width of about 0.75-1.10 mm, i.e., considerably larger than that for the highest transmission d=240 μm. A gap width of 800 μm was selected to restrict the detection volume to 100 nL.

Example 2

Measurement of Optical Loss in a Fiber Loop Cavity

In this example further investigations were based on the fact that deoxyribonucleic acid (DNA) and ribonucleic acid (RNA) can be distinguished and quantified using optical absorption measurements at 260 nm and 280 nm. The absorption ratio A260/A280 can be used to quantify nucleic acid contamination of protein samples and protein contamination of nucleic acids. For pure DNA samples the ratio is typically A260/A280=1.7 to 2.0, and A260/A280=1.5 to 2.0 for RNA. If the sample contains proteins or phenols, which have a strong absorption feature at 280 nm, the A260/A280 ratio is considerably smaller. State-of-the-art in DNA/RNA quantification and protein contamination involves UV-spectrometry on sample volumes in the microliter to milliliter range. In most absorption spectrometers the sample is placed in a cuvette, which requires sample volumes of typically tens of microliters. In many applications, however, sample volumes can be considerably lower and alternative detection methods are needed.

Figure 7A:
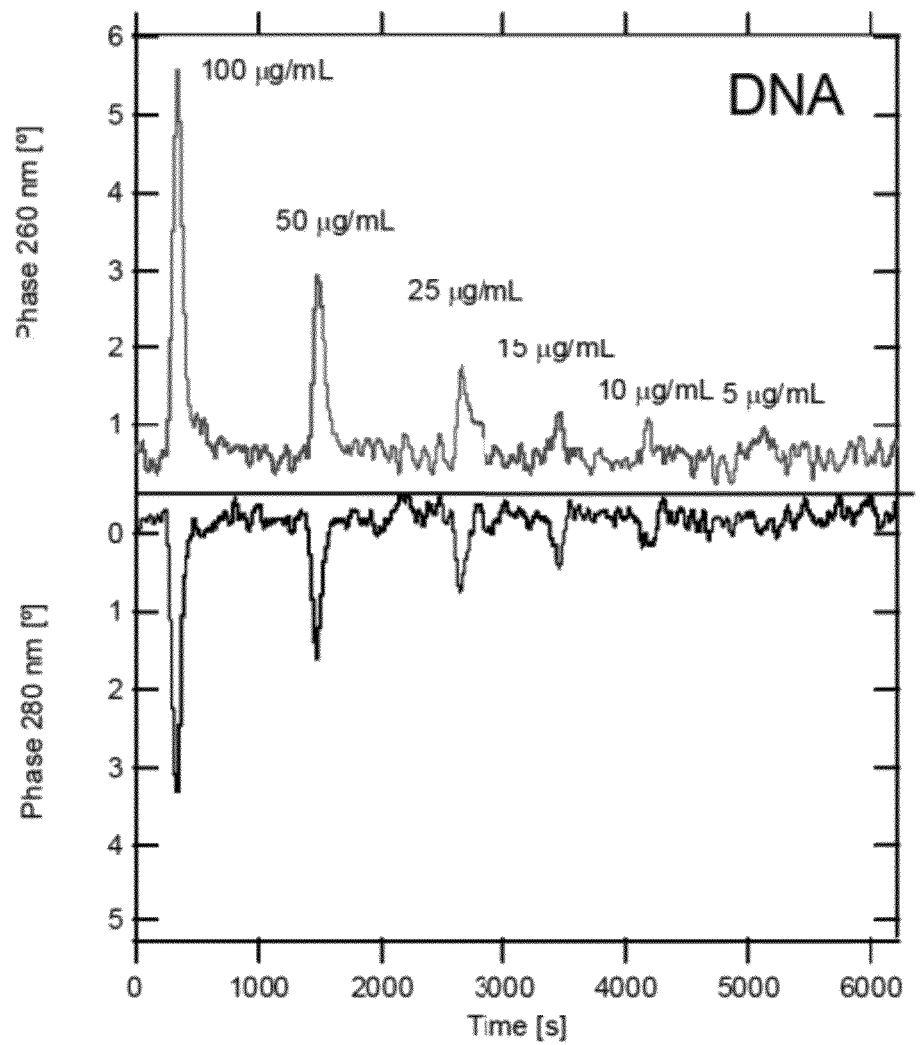
FIGS. 7(a) and 7(b) show simultaneous detection of absorption of (a) DNA and (b) RNA at 260 and 280 nm with phase-shift fiber loop CRD spectroscopy using two LEDs modulated at 1.1 and 1.0 MHz respectively.
Figure 7B:
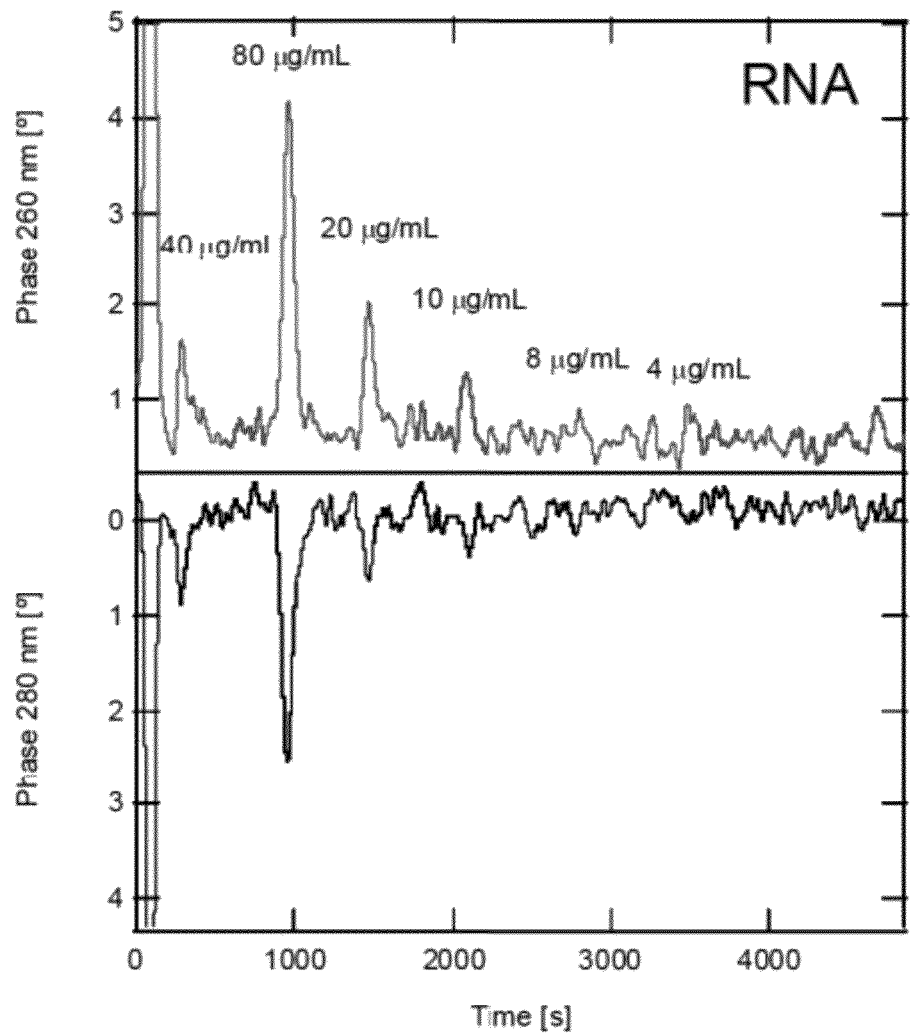

In a preliminary experiment the operating range of the fiber loop ring-down setup described above and shown in FIG. 1(a) was extended to UV wavelengths. Simultaneous dual-wavelength detection at 260 nm and 280 nm was achieved by modulating two fiber coupled LEDs at frequencies of 1.1 MHz and 1.0 MHz, respectively. The combined signal from the loop was detected using a UV enhanced PMT detector. As before, demodulating the signal with lock-in amplifiers at the corresponding frequencies allowed the cavity-induced phase-shift of each light source to be extracted. Hence, the absorbance at both wavelengths was quantified simultaneously allowing the determination of the A260/A280 ratio. FIGS. 7(a) and 7(b) show simultaneous detection of absorption at 260 and 280 nm of DNA and RNA samples prepared in a buffer solution (pH 8.3) and 5 μL sample volumes were injected at 10 μL/min. The phase shifts were sampled at a data acquisition rate of 10 Hz and a running average of 10 s was transferred to the computer. The detection volume was 100 nL. In one measurement a detection limit of 10 μg/mL was achieved at a wavelength of 260 nm in a detection volume of 100 nL.

Ketoprofene, (RS)2-(3-benzoylphenyl)-propionic acid, was also used as a more stable substitute for the nucleic acids to determine the A260/A280 ratio. A ratio of the change in the phase-shift due to the absorption of $\Delta\phi(260)/\Delta\phi(280)=1.6\pm0.1$ was determined. FIGS. 8(a) and 8(b) show results of phase shift measurements at λ=260 nm and 280 nm during multiple injections of ketoprofen (15 μg/mL). The system exhibited excellent reproducibility of the absorption signal. The $\Delta\phi 260/\Delta\phi 280$ ratio was 1.6 with a standard deviation of 0.1.

This work indicates that phase-shift fiber-loop ring-down is an effective technique for measuring and characterizing small samples even when low-finesse cavities are used. Advantages of the cavity-enhanced absorption measurement include high data acquisition rate and immunity against fluctuations of the light source intensity or detector response. The cavity enhancement of the effective absorption path lowers the detection limit, and may be improved by further reduction of the optical losses across the sample gap.

All cited publications are incorporated herein by reference in their entirety.

EQUIVALENTS

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

The invention claimed is:

1. A method for multi-wavelength cavity ring-down spectroscopy; comprising:
    simultaneously and continuously irradiating an optical cavity with light at two or more different wavelengths, each light being intensity-modulated at a different modulation frequency;
    detecting the light of two or more wavelengths after the light has traveled through the optical cavity;
    measuring an optical loss of each detected light; and
    determining a characteristic of the optical cavity from the optical loss of each detected light;
    wherein measuring optical loss comprises measuring phase shift between light entering and exiting the optical cavity for each of the two or more wavelengths at their respective modulation frequencies.

2. The method of claim 1, wherein the optical cavity comprises an optical fiber loop, a fiber Fabry-Perot cavity, a mirror cavity, a micro-photonic resonator, or a prism cavity.

3. The method of claim 1, comprising frequency-division multiplexing of the light at two or more different wavelengths.

4. The method of claim 1, wherein the optical cavity includes at least one sensor element.

5. The method of claim 4, wherein optical transmission of the at least one sensor element changes as a function of an external stimulus.

6. The method of claim 5, wherein the change in optical transmission is a change in refractive index or optical absorption or optical scattering.

7. The method of claim 5, wherein the external stimulus is physical or chemical.

8. The method of claim 4, including using at least one sensor element selected from an absorption cell, a long period grating, an evanescent field block, an interferometer, and a gap in an optical fiber.

9. The method of claim 8, wherein the absorption cell comprises a gap in an optical path of the light at two or more different wavelengths, the method including disposing a sample in the gap;
    wherein the sample has an optical absorption spectrum in a spectral region of the light at two or more different wavelengths.

10. The method of claim 9, comprising measuring absorption of the sample at the two or more wavelengths, wherein absorption is indicative of presence and/or concentration of at least one analyte in the sample.

11. The method of claim 9, wherein the sample is a gas, liquid, solid, or solid suspension.

12. The method of claim 1, wherein the optical cavity comprises an optical fiber loop.

13. Apparatus for multi-wavelength cavity ring-down spectroscopy; comprising:

an optical cavity;

two or more light sources of different wavelengths, each light being intensity-modulated at a different modulation frequency;

a detector that detects the light of two or more wavelengths after the light has traveled through the optical cavity; and a processor that measures an optical loss of each detected light;

wherein measuring optical loss comprises measuring phase shift between light entering and exiting the optical cavity for each of the two or more wavelengths at their respective modulation frequencies.

14. The apparatus of claim 13, wherein the optical cavity comprises an optical fiber loop, a fiber Fabry-Perot cavity, a minor cavity, a micro-photonic resonator, or a prism cavity.

15. The apparatus of claim 13, wherein the optical cavity includes at least one sensor element.

16. The apparatus of claim 15, wherein optical transmission of the at least one sensor element changes as a function of an external stimulus.

17. The apparatus of claim 15, including at least one sensor element selected from an absorption cell, a long period grating, an evanescent field block, an interferometer, and a gap in an optical fiber.

18. The apparatus of claim 17, wherein the absorption cell comprises a gap in an optical path of the light at two or more different wavelengths, the gap accommodating a sample disposed therein;

wherein the sample has an optical absorption spectrum in a spectral region of the light at two or more different wavelengths.

19. The apparatus of claim 13, wherein the optical cavity comprises an optical fiber loop.

* * * * *